United States Patent [19]
Maier et al.

[11] Patent Number: 4,857,462
[45] Date of Patent: Aug. 15, 1989

[54] PROCESS FOR OBTAINING D(+)-NAPROXEN

[75] Inventors: Josef Maier; Manfred Gloger, both of Weilheim; Detlef V. Hoerschelmann, Wielenbach; Jan Strejcek, Iffeldorf; Sebastian Heimerl, Tutzing, all of Fed. Rep. of Germany

[73] Assignee: Boehringer Mannheim GmbH, Mannheim-Waldhof, Fed. Rep. of Germany

[21] Appl. No.: 924,140

[22] Filed: Oct. 27, 1986

Related U.S. Application Data

[63] Continuation of Ser. No. 680,984, Dec. 12, 1984, abandoned.

[30] Foreign Application Priority Data

Dec. 16, 1983 [DE] Fed. Rep. of Germany ....... 3345660

[51] Int. Cl.$^4$ .................... C12N 9/18; C07P 41/00
[52] U.S. Cl. ...................................... 435/197; 435/280
[58] Field of Search ............................... 435/280, 197

[56] References Cited

PUBLICATIONS

Iriuchijima et al; Agric. Biol. Chem., 45(6) (1981), pp. 1389–1392.

*Primary Examiner*—Leonard Schenkman
*Assistant Examiner*—Joseph A. Lipovsky
*Attorney, Agent, or Firm*—Felfe & Lynch

[57] ABSTRACT

A process for obtaining D-2-(6-methoxy-2-naphthyl)-propionic acid from a mixture of D- and L-2-(6-methoxy-2-naphthyl)-propionic acid lower alkyl esters is provided by asymmetric hydrolysis of the L-ester with a microbial enzyme, separation of the 2-(6-methoxy-2-naphthyl)-propionic acid from the D-2-(6-methoxy-2-naphthyl)-propionic acid lower alkyl ester and saponification of the latter, wherein the saponification is carried out enzymatically with esterase from hog liver or from *Pleurotus ostreatus*.

16 Claims, No Drawings

PROCESS FOR OBTAINING D(+)-NAPROXEN

This application is a continuation of application Ser. No. 680,984 filed Dec. 12, 1984, now abandoned.

The present invention is concerned with a process for the preparation of D-2-(6-methoxy-2-naphthyl)-propionic acid, which has the following structural formula:

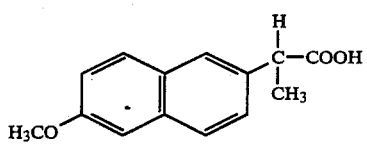

This compound is a therapeutic agent with an anti-inflammatory activity which is also known as D(+)-naproxen.

It is known to obtain the optically pure D-form from the racemic D,L-mixture with the help of optically-active amine bases, for example cinchonidine, according to the conventional methods of racemate separation (see Federal Republic of Germany Patent Specification No. 21 59 011). This Patent Specification also describes the chemical splitting of optically-active naproxen esters which is carried out by heating for 18 hours at 50° C. with sodium hydroxide in methanol, the yield obtained being from 60 to 70%.

It is also known to separate the racemic mixture by the selective splitting of the corresponding methyl ester with the help of *Aspergillus sojae* (IAM 2031), the L(−)-form of the ester thereby being preferentially split (Agric. Biol. Chem., 45 (6), 1389–1392/1981). This ester splitting, which only gives very poor yields of about 32%, gives the L(−)-form but the obtaining of the D(+)-form is not described.

It is an object of the present invention to provide a process for obtaining (D(+)-naproxen which proceeds more selectively and more simply than the known processes and makes possible a practically complete conversion of the racemate into the desired D(+)-form.

Thus, according to the present invention, there is provided a process for obtaining D-2-(6-methoxy-2-naphthyl)-propionic acid from a mixture of D- and L-2-(6-methoxy-2-naphthyl)-propionic acid lower alkyl esters by the asymmetrical hydrolysis of the L-ester with a microbial enzyme, separation of the 2-(6-methoxy-2-naphthyl)-propionic acid from the D-2-(6-methoxy-2-naphthyl)-propionic acid lower alkyl ester and saponification of the latter, wherein the saponification is carried out enzymatically with esterase from hog liver or from *Pleurotus ostreatus*.

The present invention is based upon the surprising discovery that D-lower alkyl esters of naproxen are split quantitatively by hog liver esterase and thus a completely enzymatic process is made possible which, starting from the lower alkyl esters of racemic naproxen, leads directly to the desired product. Esterase from *Pleurotus ostreatus* possesses the same property. Esterases of other origins have proved to be unsuitable. By means of the process according to the present invention, D(+)-naproxen is obtained with an optical purity of 98%.

The hog liver esterase or the *Pleurotus ostreatus* esterase is preferably used in immobilised form in the process according to the present invention. For the immobilisation, there can be used the methods of carrier fixing which are well known to the expert, for example fixing with cyanogen bromide-activated carriers based on polymeric carbohydrates, such as dextrans, starches, cellulose and the like, cross-linking with bifunctional bridge formers, such as glutardialdehyde, diepoxides and the like, adsorption on insoluble carriers or by means of the process of enzyme copolymerisation, such as is described, for example, in Federal Republic of Germany Patent Specifications Nos. 21 28 743 and 22 60 185. The latter process is preferred. Hog liver esterase is known and can be isolated and purified according to known methods.

The first step of the process according to the present invention can be carried out in known manner with the use of the enzyme from *Aspergillus sojae*, IAM 2031. However, better results are obtained with the use of a specific splitting esterase from *Aspergillus oryzae*, DSM 2808 (ATCC 11492), *Aspergillus flavus*, DSM 2807, *Aspergillus sojae*, DSM 2809, or *Bacillus subtilis*, DSM 2806. These enzymes give a better selectivity of the splitting reaction and display a high activity. The enzymes can be employed in purified form or also in the form of the undisrupted micro-organisms. In particular, it is possible to contact the mycelium of the said strains of Aspergillus directly with the racemic ester mixture. Alternatively, previously purified esterase can be used, preferably also in carrier-fixed form. The above statements regarding the carrier fixing of the hog liver esterase apply in the same way to the microbial esterase of the first step of the process. The microbial esterase is preferably obtained by disruption of the micro-organism in the usual manner in the presence of a tenside or, more preferably, after pre-treatment with a tenside. The soluble fraction of the disrupted micro-organism can then be pre-purified according to conventional methods, for example by chromatography over a weakly basic anion exchanger.

As already mentioned, the lower alkyl esters of naproxen are accessible to the asymmetric hydrolysis. By lower alkyl esters are here to be understood the esters of alcohols with up to 4 carbon atoms, the methyl and ethyl esters being preferably used.

The mixture of D(+)-naproxen ester and L(−)-naproxen obtained by the selective hydrolysis can easily be separated quantitatively by separating the salts of naproxen acid from the insoluble ester, the separation taking place most simply by filtration or centrifuging. The pure D(+)-ester thus obtained is then contacted with the hog liver esterase or esterase from *Pleurotus ostreatus*, the free acid thereby being obtained with an optical purity of about 98%.

According to a preferred embodiment of the process of the present invention, the D(+)-naproxen is obtained continuously, the racemic ester mixture thereby first being split selectively with the microbial esterase, the D(+)-ester and the L(−)-acid are separated, preferably continuously, the separated L(−)-acid is racemised, the racemate obtained is converted into the lower alkyl ester and the racemic ester mixture is recycled for splitting with microbial esterase. The D(+)-ester remaining in the solution in the case of the separation of ester and acid is contacted with esterase from hog liver or from *Pleurotus ostreatus*, with the liberation of the D(+)-acid, without change of the steric configuration. This preferred embodiment of the process according to the present invention preferably uses the enzymes in both steps in immobilised form. In the first step, it has hereby proved to be especially preferred to use Aspergillus mycelium pre-treated with bifunctional cross-linking agents, whereas in the reactor for the second step there is preferably used the esterase obtained in insoluble form by enzyme copolymerisation.

When carrying out this preferred embodiment of the process, it is preferable to maintain a pH value of from 4 to 9 and more preferably of from 7 to 8.5 and preferably to maintain a temperature of from 10° to 50° C. and more preferably of from 30° to 45° C.

An especial advantage of this embodiment of the process according to the present invention is that, by means of the continuous method operating, with separation of the L-acid and D-ester after the first step, the alcohol split off, which acts as inhibitor for the enzyme of the first step, is continuously removed and, at the same time, high substrate concentrations can be maintained, which avoids the danger that, towards the end of the reaction, the L-ester is no longer split quantitatively due to the decreasing substrate concentration.

The enzyme of the first step splits the L-form of the ester quantitatively but also attacks a small part of the D-ester. However, due to the subsequent racemisation, this D-ester is not lost but is again returned to the splitting step so that a practically quantitative conversion of the racemic naproxen into D(+)-naproxen is achieved.

Esterification of the naproxen can be carried out by conventional methods, for example by heating in the particular alcohol chosen in the presence of an acidic catalyst, such as toluenesulfonic acid. Since the ester formed is sparingly soluble in the alcohol, it can easily be separated and introduced into the selective ester splitting step. The enzyme of the above-mentioned preferably used Aspergillus strains can be used in the form of the undisrupted mycelium, preferably cross-linked with difunctional reagents, such as glutardialdehyde, or can be used in purified form. For the purification, it has proved to be preferable to carry out an extraction in the presence of a surface-active agent (tenside), especially after a pre-treatment therewith. Appropriate methods of lysis include, for example, use of an ultra-sonifier, class bead milling, grinding in a mortar and pestle or using a high-speed homogenizer. Appropriate surface-active agents include, for example, polyoxyethylene derivatives, such as disorbitan fatty acid esters, sorbitan monooleate, glycerol monolaurate, lanolin alcohol derivatives, sulfosuccinic acid hemiesters of oxylated lauryl alcohol, lauryl ether sulfate salts and the like.

The enzyme obtained from the preferred microorganism Aspergillus oryzae DSM 2808 (ATCC 11492) displays an activity maximum at pH 8 and at pH 5 still has about 65% of the activity at the pH optimum. The $K_M$ was found to be $2.2 \times 10^{-3}$. The specific activity in the lyophilised mycelium is about 5.5 U/g. The enzyme activities are measured in an autotitrator with the substrate D,L-naproxen methyl ester at 25° C. and pH 7.8. One unit (U) corresponds to the reaction of 1 µmole/minute.

The following Examples are given for the purpose of illustrating the present invention:

EXAMPLE 1

(A) Preparation of the ester 20 g. of racemic naproxen are heated under reflux for 4 hours with 0.5 g. toluenesulfonic acid in 200 ml. methanol. After cooling to 4° C., the crystalline slurry formed is filtered off with suction and subsequently washed with a little cold methanol. The yield is 19.5 g.

(B) Selective ester splitting 3.0 g of lyophilised mycelia of *Aspergillus oryzae* DSM 2808 (ATCC 11492) are suspended in 50 ml. of water and stirred to pH constancy (7.8). After the addition of 1 ml. polyethylene glycol monobutyl ether, 4 g. of the D,L-naproxen methyl ester obtained according to (A) are added thereto. The pH value is kept constant at 7.8 by the addition of 0.2M sodium hydroxide solution. L-Naproxen formed goes into solution as salt and is continuously separated from the reaction solution by filtration, the temperature being 40° C.

After completion of the reaction, the D-naproxen methyl ester is removed from the reaction mixture by extracting twice with, in each case, 50 ml. n-pentane, the solvent is evaporated and the residue is resuspended in 50 ml. of water.

500 mg. of esterase from hog liver (EC 3.1.1.1) are dissolved in 40 ml. of water and the suspension of the D-naproxen ester is added thereto. The suspension is then stirred at 32° C. and at pH 7.2 until the splitting is complete. For maintaining the pH value constant, a total of 9 ml. 0.1N aqueous sodium hydroxide solution are added. The pH value is then adjusted 1.5 with 2N hydrochloric acid and the precipitated D-naproxen can be removed. The precipitate is extracted with ethanol. Thus 1.52 g. of pure D(+)-naproxen can be obtained.

EXAMPLE 2

(A) Culturing of *Aspergillus oryzae*, DSM 2808 (ATCC 11492).

Medium:
0.5% peptone from casein (Merck)
0.5% peptone from meat (Merck)
2% glucose
1% maltose
pH 5.4, demineralized water
Fermentation parameters:
temperature 28° C.
agitation 300 r.p.m.
aeration 300 liters/hour in a 10 liter fermenter
pH maintenance at least pH 4.0 with 10% aqueous potassium hydroxide solution
anti-foaming agent 10% Wacker silicone First state of inoculum growth Inoculum from slaut agar suspended in 5 ml. Sabouraud medium (roller tube culture) incubated for 48 hours at 28° C.

Second stage of inoculum growth 100 ml. Sabouraud medium inoculated with the above sead culture (500 ml. Erlenmeyer flask with one baffle). Incubation for 48 hours at 28° C. and 180 r.p.m.

Third stage of inoculum growth 900 ml. Sabouraud medium inoculated with the second seed culture (2000 ml. Erlenmeyer flask with magnetic stirrer). Incubation for 70 hours at 28° C. while stirring.

This culture forms an inoculum for 10 liter fermenter.
Culture period: 96 to 120 hours.
Harvesting: by means of a filter with a 100 µm. pore size.
Yield: 870 g. of wet mass = 123 g. dry mass.

(B) Preparation of carrier-fixed esterase from *Aspergillus oryzae.*

The mycelium obtained according to (A) is mixed with polyoxyethylene sorbitan monooleate up to an end concentration of 0.04% and solubilised after 6 hours in a high pressure press (Manton/Gaulin). Insoluble material is removed and the supernatant chromatographed over a weakly basic cation exchanger (DEAE-Sephadex G 50). The active fractions are combined and then contain 6 U/ml.

5 ml. of the pre-purified esterase preparation are stirred for 30 minutes at 10° C. with 60 mg. methacrylic acid-N-hydroxysuccinimide ester dissolved in 1.2 ml. dioxan. A solution consisting of 1.8 g. acrylamide, 0.3 g. N,N-methylene-bis-acrylamide and 15 ml. 0.2M TRAP buffer (pH 8.0) is then added thereto. After cooling to 5° C. and adding 1 ml. of 10% ammonium peroxydisulfate solution and 1 ml. 10% 3-dimethylaminopropionitrile in water, the reaction mixture is gassed with nitrogen up to the commencement of the polymerisation.

The gel obtained is, after 3 hours, pressed through a sieve with a mesh size of 0.3 mm. and washed first with 0.5M phosphate buffer (pH 7.5) and then with distilled water and thereafter lyophilised.

There is thus obtained carrier-bound esterase with a specific activity of 3.6 U/g.

When repeating the process but without the 30 minutes pre-incubation, there is obtained a carrier-fixed esterase with a specific activity of 1.8 U/g.

The above-described process is repeated with the use of acrylic acid chloride (30 μl. in 1 ml. diethyl ether) instead of methacrylic acid N-hydroxysuccinimide ester. The resulting carrier-fixed esterase has a specific activity of 2.4 U/g.

(C) Preparation of carrier-fixed hog liver esterase

The procedure described under (B) is used, with the use of 40 ml. hog liver esterase c=10, 20 ml. 0.2M Tra/HCl buffer (pH 8.4) and 400 mg. methacrylic acid N-hydroxysuccinimide ester, dissolved in 2 ml. dioxan. After a pre-incubation of 30 minutes, there is added a solution of 10 g. acrylamide, 2.5 g. N,N-methylene-bis-acrylamide, 40 ml. 0.2M Trap/HCl buffer (pH 8.4), 3 ml. 20% ammonium peroxydisulfate solution and 3 ml. 20% dimethylaminopropionitrile solution and the reaction is carried out as described under (B).

The carrier-fixed hog liver esterase obtained has a specific activity of 20 U/g.

(D) Racemic naproxen methyl ester, prepared in the manner described in Example 1, is introduced at a rate of 0.1 g./hour in the form of a 2% aqueous solution with a pH of 7.8 into a 100 ml. reactor which contains the carrier-fixed esterase of *Aspergillus oryzae* obtained as described under (B), the pH value being kept constant by the addition of 0.2N aqueous sodium hydroxide solution. L-Naproxen sodium salt formed is filtered off continuously and, after racemisation and esterification, again returned to the reactor. After separating off the carrier-fixed enzyme, the filtered reaction mixture is passed to a second reactor which contains 1 g. of the carrier-fixed hog liver esterase obtained according to (B), suspended in 50 ml. water. The pH value is kept constant at 7.3 by the addition of 0.2N aqueous sodium hydroxide solution. D-Naproxen formed is precipitated out of the reaction solution with 0.5N hydrochloric acid, washed twice and dried.

Yield: 98%; $[\alpha]_D^{22} = 66.1°$ (c=0.5 in chloroform).

EXAMPLE 3

Preparation of esterase (extract) from *Pleurotus ostreatus*

1 g. dried *Pleurotus ostreatus* is lysed, extracted with 50 ml. 100 mM phosphate buffer (pH 7.3), dialysed against 10 mM phosphate buffer (pH 7.3) for 12 hours and lyophilised. The yield is 400 mg.

This extract can be used instead of the esterase from hog liver in the manner described in detail in Examples 1 and 2.

We claim:

1. A process for obtaining D-2-(6-methoxy-2-napthyl)-propionic acid from a mixture of D- and L-2-(6-methoxy-2-naphthyl)-propionic acid lower alkyl esters comprising contacting said mixture with a sample of microorganisms which contain an enzyme which asymmetrically hydrolyzes said L-ester said microorganisms selected from the group consisting of *Aspergillus oryzae* DSM 2808 (ATCC 1192), *Aspergillus flavus* DSM 2807, *Aspergillus sojae* DSM 2809, and *Bacillus subtilis* DSM 2806 under conditions favoring asymmetric hydrolysis of said L-ester to a corresponding L-acid, separating the L-2-(6-methoxy-2-naphthyl)-propionic-acid from the D-(6-methoxy-2-naphthyl)-propionic acid lower alkyl ester and saponifying said D-ester free of L. ester with an esterase from pig liver or from *Pleurotus ostreatus* by contacting said D-ester with said enzyme under conditions favoring saponification to said D-acid.

2. The process of claim 1, wherein there is used carrier-fixed esterase from hog liver or from *Pleurotus ostreatus.*

3. The process of claim 1, wherein the asymmetric hydrolysis is carried out with an esterase from *Aspergillus oryzae* DSM 2808 (ATCC 11492), *Aspergillus flavus* DSM 2807, or *Bacillus subtilis* DSM 2806.

4. The process of claim 3, wherein the esterase is obtained from the microorganism by treating the microorganism with a tenside and then disrupting the microorganism and purifying the soluble fraction of the disrupted microorganism.

5. The process of claim 3 wherein there is used mycelium from *Aspergillus oryzae* DSM 2808 (ATCC 11492) treated with a bifunctional cross-linking agent.

6. The process of claim 5, wherein there is maintained a pH value of from 4 to 9.

7. The process of claim 6 wherein a temperature of from 10° to 50° C. is maintained.

8. The process of claim 6, wherein there is maintained a pH value of from 7 to 8.5.

9. The process of claim 8 wherein a temperature of from 30° to 45° C. is maintained.

10. The process of claim 6 wherein a temperature of from 10° to 50° C. is maintained.

11. The process of claim 10, wherein there is maintained a temperature of from 30° to 45° C.

12. The process of claim 1 wherein D-2-(6-methoxy-2-naphthyl)-propionic acid lower alkyl ester and L-2-(6-methoxy-2-naphthyl)-propionic acid are continuously separated, the L-2-(6-methoxy-2-naphthyl)-propionic acid is racemised, the racemate formed is esterified and the racemic ester mixture is to the splitting step with said esterase.

13. The process of claim 12 wherein a temperature of from 10° to 50° C. is maintained.

14. Process of claim 1, wherein said esterase is from *Pleurotus ostreatus.*

15. Process for obtaining D-2-(6-methoxy-2-naphthyl)-propionic acid from a mixture of D and L-2-(6-methoxy-2-naphthyl)-propionic acid lower alkyl esters comprising contacting said mixture with a sample of microorganisms which asymmetrically hydrolyzes said L-ester under conditions favoring asymmetric hydrolysis of said L-ester to a corresponding L-acid, separating the L-2-(6-methoxy-2-naphthyl)-propionic acid from the D-(6-methoxy-2-naphthyl)-propionic acid lower alkyl ester and saponifying said D-ester free of L-ester with an esterase from pig liver or from *Pleurotus ostreatus* by contacting said D-ester with said enzyme under conditions favoring saponification to said D-acid.

16. Process of claim 15, wherein said esterase is from *Pleurotus ostreatus*.